United States Patent [19]

Galy et al.

[11] Patent Number: 4,729,208
[45] Date of Patent: Mar. 8, 1988

[54] METHOD AND APPARATUS FOR PREPARING SYRINGES CONTAINING A LYOPHILE MEDICINE

[76] Inventors: Michel Galy, Le Blein St Loup, 69490 Pontchara Sur Turdine; Alain Genet, 16, rue du Prieuré, 69130 Ecully, both of France

[21] Appl. No.: 65,652

[22] Filed: Jun. 25, 1987

Related U.S. Application Data

[63] Continuation of Ser. No. 933,272, Nov. 20, 1986, abandoned, which is a continuation of Ser. No. 680,053, Dec. 10, 1984, abandoned.

[30] Foreign Application Priority Data

Dec. 8, 1983 [FR] France .................... 83 19667

[51] Int. Cl.$^4$ .................... B65B 31/00
[52] U.S. Cl. .................... 53/432; 53/440; 53/510; 53/127; 53/328
[58] Field of Search .................... 34/5; 53/154, 167, 202, 53/428, 432, 433, 111 R, 510, 511, 127, 319, 322, 324, 328

[56] References Cited

U.S. PATENT DOCUMENTS

| | | | |
|---|---|---|---|
| 3,245,194 | 4/1966 | Carski | 53/489 X |
| 3,470,675 | 10/1969 | Crane | 53/202 X |
| 3,737,973 | 6/1973 | Stawski | 53/489 X |
| 4,233,799 | 11/1980 | Caille | 53/154 |
| 4,286,389 | 9/1981 | Ogle | 34/5 |

FOREIGN PATENT DOCUMENTS

| | | | |
|---|---|---|---|
| 1374715 | of 1964 | France | 34/5 |
| 1499456 | 2/1978 | United Kingdom | 34/5 |

*Primary Examiner*—Robert L. Spruill
*Assistant Examiner*—Steven P. Weihrouch
*Attorney, Agent, or Firm*—Cushman, Darby & Cushman

[57] ABSTRACT

A series of syringe bodies with their lower ends closed is filled with a solution of medicine to a predetermined level in the bodies. The syringe bodies are placed in a lyophilizer with the bodies arranged in a predetermined pattern. A plurality of plungers for the syringe bodies is arranged in a corresponding pattern and above the syringe bodies. After the medicine in the syringe bodies is lyophilized in the lyophilizer, a reduced pressure is created in the lyophilizer and the plungers are simultaneously moved into the syringe bodies to a predetermined level above the lyophilized medicine. The pressure within the lyophilizer is then increased to atmospheric and the assembled syringes are removed. Apparatus for implementing the process can include a lower rack having openings for retaining the syringe bodies in the predetermined pattern, and an upper rack seatable on the lower rack for retaining the piston portions of plungers in facing relation to, aligned with, and above the openings of the syringe bodies. A mechanism within the lyophilizer can be used to simultaneously push the plungers downwardly into the lyophile medicine-containing syringe bodies.

5 Claims, 9 Drawing Figures

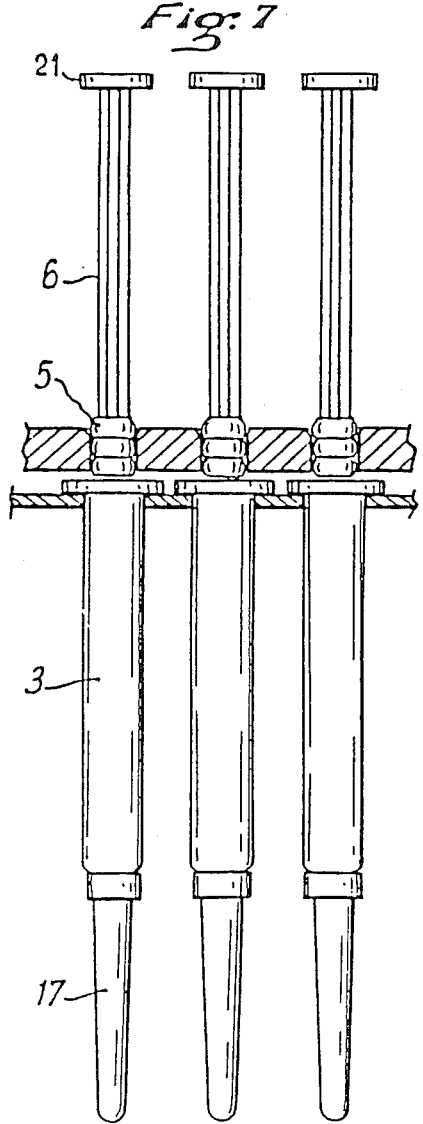
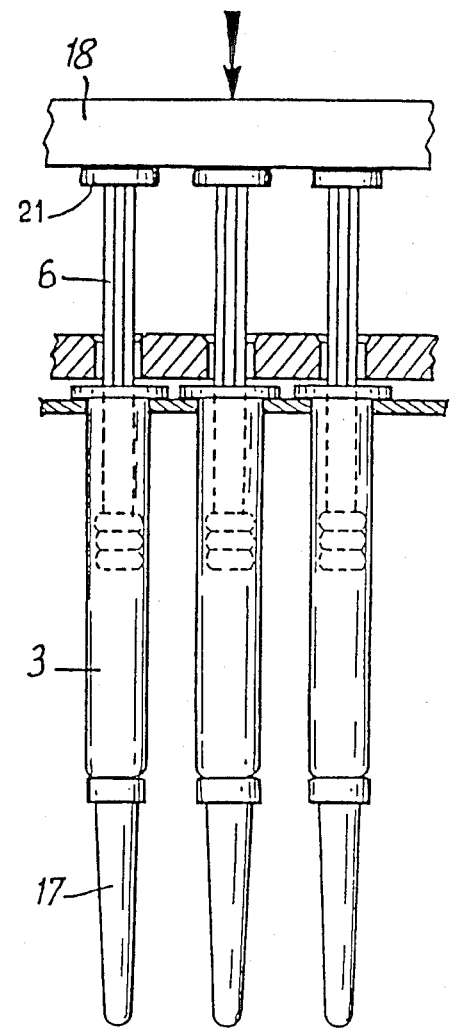
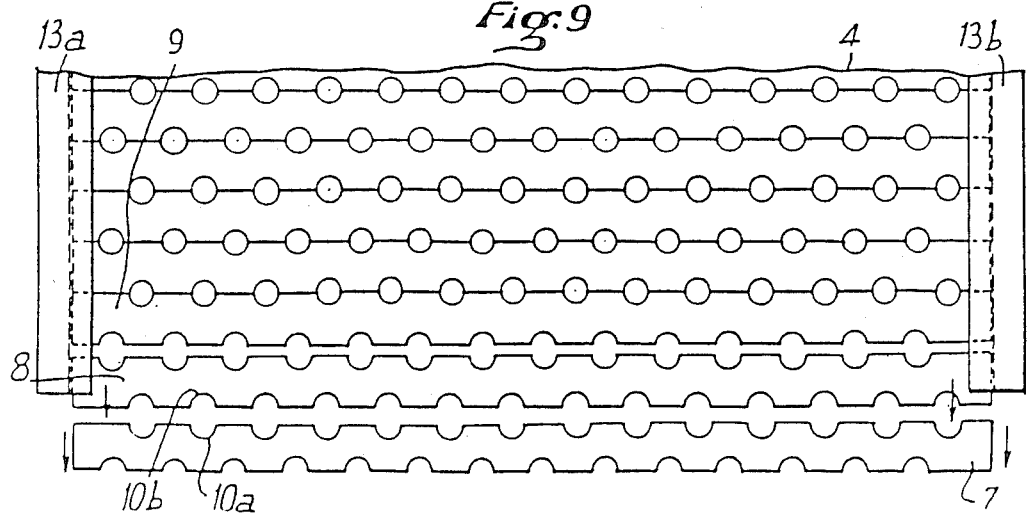

METHOD AND APPARATUS FOR PREPARING SYRINGES CONTAINING A LYOPHILE MEDICINE

This is a continuation of application Ser. No. 933,272, filed Nov. 20, 1986, which was abandoned upon the filing hereof and which was a continuation of application Ser. No. 680,053, filed Dec. 10, 1984, (now abandoned).

An object of the present invention is a process for preparing a series of auto- or self-injectable syringes containing a lyophile medicine, as well as apparatus for implementing this process.

BACKGROUND OF THE INVENTION

Lyophile vaccines are already available in the form of single doses in auto-injectable containers, these containers including a flexible tube or bag constituting an auto-injectable syringe without a piston (see, for example, U.S. Pat. No. 4,022,206).

The present invention relates to a process for preparing single doses of lyophile medicine in auto-injectable syringes of the type having an injection piston.

The preparation of a series or group of auto-injectable syringes containing a lyophile medicine presents difficulties because the lyophilization must be done while the syringes are open and the closing or sealing of the syringes with the pistons presents difficulties due to the presence of gas trapped in the syringe, which, in practice, requires this closing or sealing to take place inside the lyophizer apparatus itself.

SUMMARY OF THE INVENTION

The present invention has as an object a process which avoids the previous difficulties and provides auto-injectable syringes containing a lyophile medicine by simple operations under optimum conditions of uniformity and sterility.

The present invention has as an object a process for preparing a series or group of auto-injectable syringes containing a lyophile medicine, the syringes being of the type having a cylindrical syringe body whose lower end is adapted to receive an injection needle, and a plunger having a rod with an enlarged lower end forming a piston, usually of a resilient or elastic material which slides with friction within the tubular body. The processes or method of the invention includes:

blocking or sealing the lower ends of the tubular syringe bodies with removable seals;

positioning a number of the syringe bodies vertically on a first flat horizontal rack so that the tubular bodies extend through holes or openings in the first rack and the tubular bodies are held with their upper ends all at essentially the same level;

introducing a predetermined single dose quantity of medicine in the form of a solution in a solvent into each tubular body which is so positioned;

positioning a number of plungers equal to the number of syringe bodies on a second flat rack, by placing the lower piston ends of the plungers in holes of such a size in the second rack that the lower piston ends are frictionally held, but can be forced through the holes, the holes in the upper rack being so arranged that the holes in the upper rack are aligned respectively with the holes of the lower rack when the two racks are superimposed;

positioning the second rack carrying the plungers on top of the first rack carrying the tubular syringe bodies containing the medication solution, with the rods of the plungers extending upwardly and the piston ends facing downwardly;

fastening the racks together so that the corresponding holes are aligned with each other and the lower piston end of each plunger is above the upper end of the corresponding tubular body without sealing this upper end, to form an assembly in which the internal space above the tubular syringe bodies is open for exterior communication;

introducing the assembly into a lyophilizer apparatus;

performing lyophilization in the apparatus;

introducing an inert gas into the lyophilizer apparatus at a predetermined pressure lower than atmospheric pressure;

then applying a vertical downward force to the plungers to introduce the pistons into the corresponding tubular bodies to a predetermined maximum penetration position located above the upper level of the lyophilized medicine;

then introducing inert gas into the lyophilizer apparatus until the pressure reaches atmospheric pressure;

and removing the medicine containing auto-injectable syringes thus obtained from the first and second racks.

Particular embodiments of the process of the present invention can also include the following characteristics, alone or in combination:

the vertical thrust can be applied to the plungers by means of a cylinder in the lyophilizer apparatus;

the second rack can comprise a number of dismountable rack or cross-bar elements held against each other by means of removable clamping or tightening means, each of the holes of the second grid then comprising two half-holes or semi-circular openings formed along the length of vertical side walls of two adjacent facing rack elements, and to remove the auto-injectable syringes, the clamping means are released to permit removal of the dismountable rack elements.

The present invention also has as its object an apparatus to implement the process described above.

This apparatus which is, during use, placed on a horizontal support, includes:

a first flat rack or grid having rows of identical holes;

means for holding the first grid horizontally at a predetermined distance from the horizontal support;

a second flat removable rack pierced with holes so that each hole of the first grid corresponds coaxially with a hole of the second rack when the two racks are superimposed;

and means to maintain the second rack horizontal and at a fixed predetermined vertical distance above the first rack.

In particular embodiments the apparatus of the invention can also include the following characteristics either alone or in combination:

the cross section of the holes of the first rack are large enough to allow the passage of the tubular syringe bodies with slight play, the upper flanges of the bodies resting on the rack;

the second grid is thick enough that, when the pistons are placed in it, the holes serve as guides for the pistons, during initial displacement of the pistons downwardly under the action of the vertical thrust, and until the pistons enter the upper ends of the tubular syringe bodies;

the second rack comprises a number of dismountable rack elements pressed against each other by means of clamping or tightening means, and each of the holes of the second rack comprise two half-holes formed along the length of vertical side walls of two facing adjacent elements.

Non-limiting examples of the invention will be described in detail with reference to preferred embodiments shown in the accompanying drawings.

BRIEF DESCRIPTION OF DRAWINGS

FIG. 7 is a partial view in elevation showing the relative positions of the pistons and the syringe bodies in the assembled apparatus during the lyophilization operation;

FIG. 8 is a partial view in elevation illustrating the simultaneous driving of the syringe pistons into the syringe bodies after the lyophilization step; and FIG. 9 is a partial plan view of the upper rack showing the cross-bar withdrawal operation after unfastening or unlocking.

DETAILED DESCRIPTION

Figure 1:
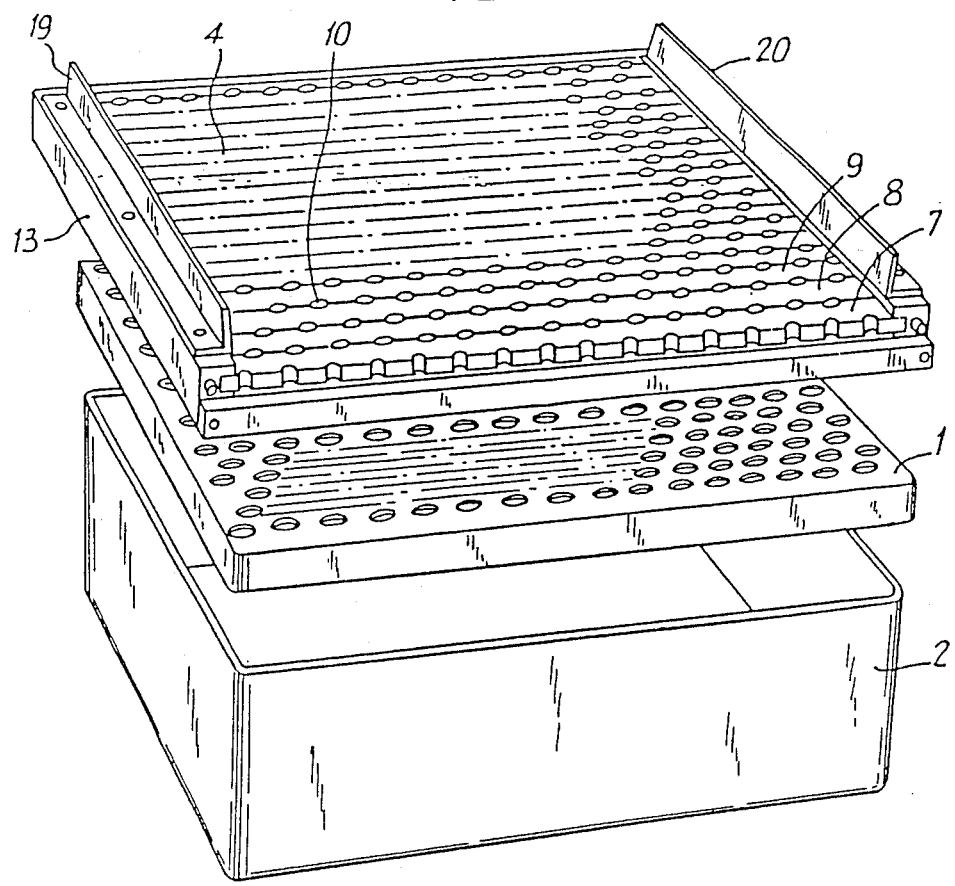
FIG. 1 is an exploded view in perspective showing an apparatus according to the invention.

The apparatus essentially includes a lower plate or rack 1 perforated with regularly spaced holes and made in the form of a cover or lid for a box or case 2 which constitutes a support for holding the plate 1 at a suitable distance above a table or other working area. The holes in the plate 1 have a diameter slightly greater than the diameter of the syringe bodies 3, but the diameter of the holes is somewhat smaller than the usual finger grip flange at the upper end of a syringe body so that the syringe body is suspended and retained in an opening by its flange.

The upper rack or grid 4 has holes of a diameter slightly smaller than the diameters of the pistons 5 of plungers 6. As can be seen at FIGS. 1, 2, 7 and 8, the holes of the lower rack 1 and of the upper rack 4 correspond with each other.

Figure 3:
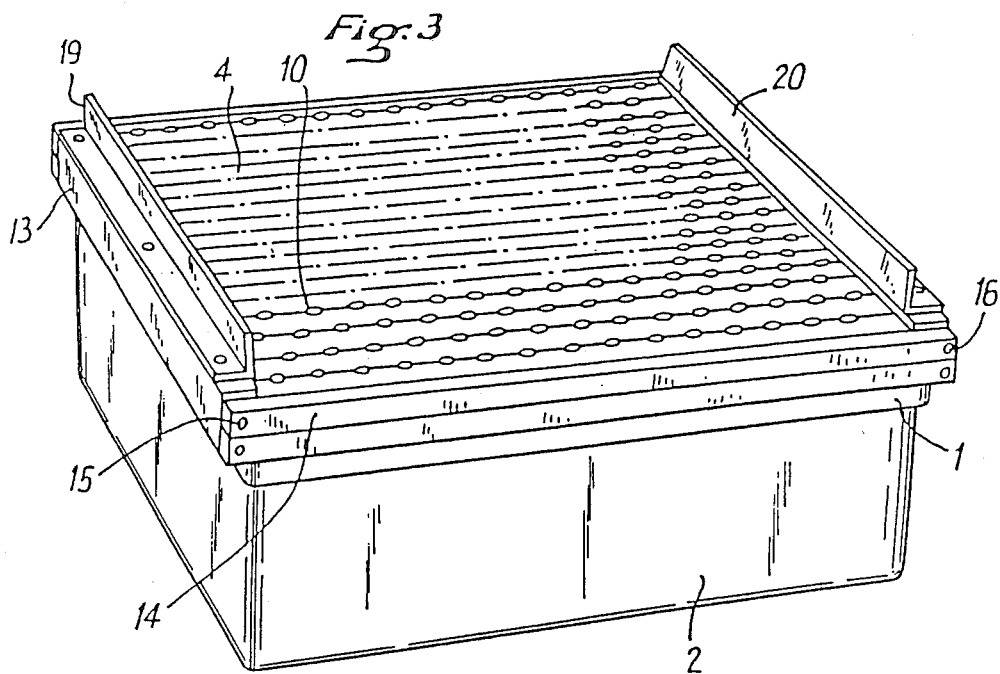
FIG. 3 is a view in perspective of the assembled apparatus.
Figure 4:
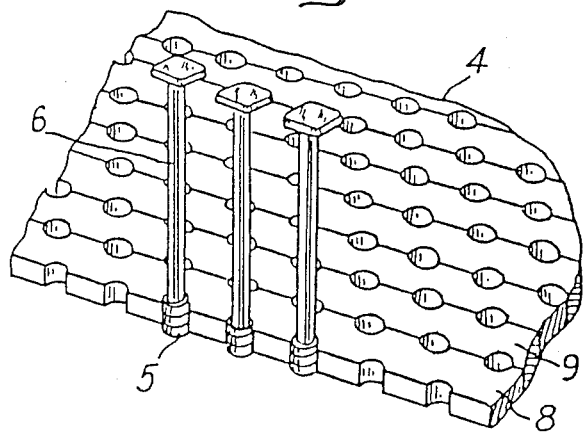
FIG. 4 is a partial view in perspective of the upper rack showing the positioning of the syringe pistons prior to the lyophilization step.
Figure 5:
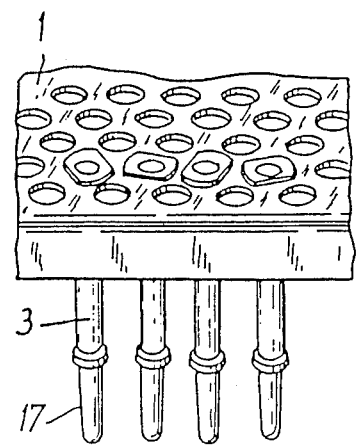
FIG. 5 is a partial pictorial view of the lower rack showing the positioning and retention of the syringe bodies.
Figure 6:
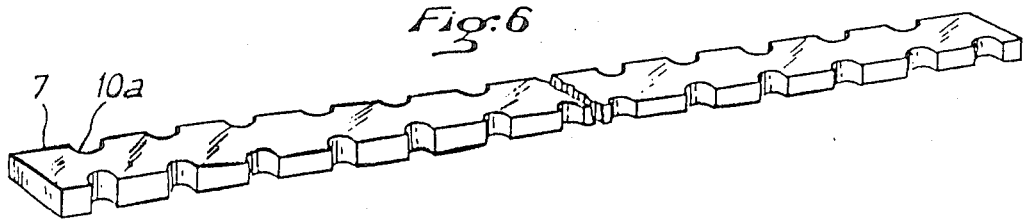
FIG. 6 is a partial pictorial view of a crossbar support element of the upper rack.

The upper rack 4 is composed of 20 cross-bars such as 7, 8, 9, etc., each hole such as 10 (FIGS. 1 and 3) being composed of two half-holes or semi-circles such as 10a, 10b (FIG. 9). As shown at FIG. 9, the semi-circular holes along one side of a cross-bar are midway between the semi-circular holes at the other side of the cross-bar to conserve space without weakening the cross-bar.

The cross-bars are inserted in spaced apart grooves 11, 12 formed in side frame members 13, and which are open at the front of rack 4. The rearward ends of grooves 11, 12 can be closed or blocked by a connecting bar which extends between and is connected to the rearward ends of the side frame members 13. The bars are held tight by the pressure of a clamp bar 14 held and forced against the cross-bars by screws 15, 16.

The piston or plug portion 5 of each plunger 6 is of a sufficient axial length to hold the plunger 6 upright in an opening of upper rack 4. The cross-bars of rack 4 are of a thickness sufficient to frictionally retain the pistons in the rack openings and to guide the pistons when they are forced downwardly. To facilitate inserting the pistons in the openings of rack 4, each opening can have a chamfered or counter-sunk upper end, as shown at FIG. 8.

In use of the rack 4, the rack is first assembled so that all the cross bars are locked and held in position by the clamp bar 14. Then, the rack is placed on a horizontal support, and the piston portion 5 of a plunger 6 is pushed downwardly into each opening 10 so that a number of plungers 6 are supported by the rack 4. If desired, a spacer plate can be placed under rack 4 to assure that each piston 5 extends the same short distance below a cross-bar of rack 4, this position being shown at FIG. 7.

Figure 2:
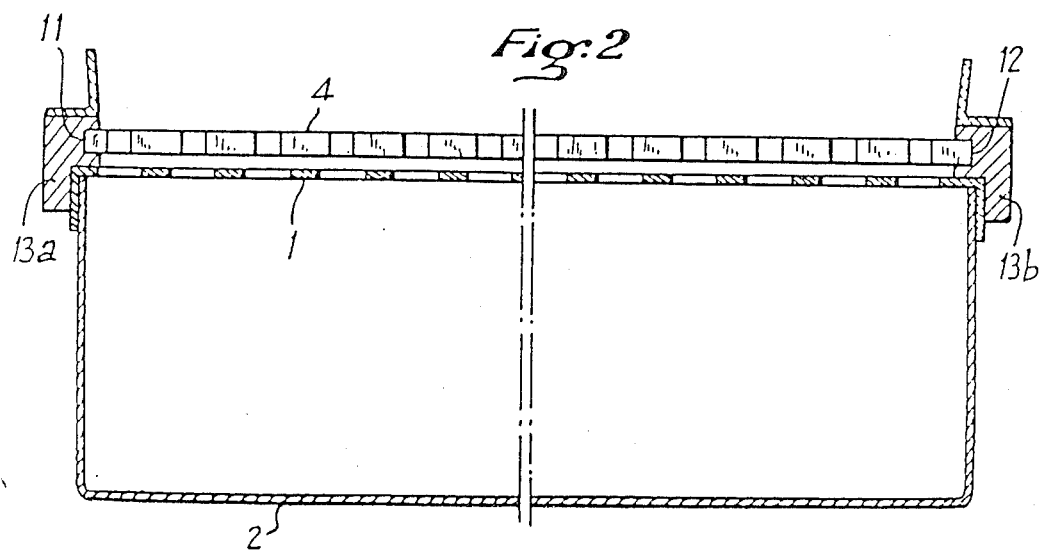
FIG. 2 is a front view in vertical section of the assembled apparatus.

The plate 1 and rack 5 are so constructed that for each hole in plate 1 there is a corresponding hole in rack 4. In addition, the side frame members 13 of rack 4 and the front and rear connecting bars of the rack cooperate with the edges of plate 1 so that each opening in rack 4 is axially aligned with an opening in plate 1 when rack 4 is seated on plate 1 as shown at FIG. 2. It will also be noticed from FIGS. 2 and 7, that when the rack 4 is seated on plate 1, the cross-bars are spaced somewhat above the top surface of plate 1, this distance being sufficient to assure that the pistons 5 do not close or otherwise obstruct the upper ends of the tubular syringe bodies. As shown at FIG. 7, when rack 4 is seated on plate 1, there is a slight space between the lower end of each piston 5 and the upper end of each syringe body 3.

The process of the invention is practiced as follows. The rack 4 is assembled and a plunger 6 is inserted in each opening in the rack, as previously described, with the piston portion 5 of each plunger being frictionally held in an opening of the rack. The piston portions 5 of the plungers are each preferably inserted to the same depth in the respective openings of rack 4. The assembled rack with the plungers so retained is then sterilized using normal precautions and procedures.

Then, a group of syringe bodies 3 are provided with needles (not shown) and needle protectors 17 and are then inserted in each hole of the lower rack or plate 1 which, for convenience, is placed on the support case 2. In a preferred form, the support case 2 is of sufficient depth that the lower end of needle protectors 17 is located 1 mm from the bottom of case 2 when plate 1 is in position on the case. This assembly of case, plate 1, and syringe bodies 3 with needle protectors 17 thereon is then sterilized.

After the syringe bodies are sterilized, a predetermined quantity of the desired medication, in solution, is dispensed into each syringe body through the open upper end of the syringe body. Such filling of the medication solution into the syringe bodies can be done manually, or can be done with an automatic dispensing pump, precautions being taken to assure sterility during filling of the medication into the syringe bodies.

The sterlized upper rack 4 with the retained plungers 6 is then seated on the assembly of case 2 and plate 1. As shown at FIGS. 2 and 7, the side frame elements 13a and 13b maintain the cross-bars of the rack 4 spaced above the upper ends of the syringe bodies 3 so that the upper ends of the syringe bodies are essentially open and unobstructed at this stage of the procedure. It is preferred that the spacing between the bottom of the cross-bars 7 and the upper surface of plate 1 be on the order of about 3 mm, although the exact spacing will depend on the thickness of the finger grip flange at the upper end of syringe body 3. Of course, the lower ends of the piston portions 5 of each plunger are spaced above the upper ends of the syringe bodies so that these pistons at this time do not obstruct the open upper ends of the syringe bodies.

The assembly of case 2, plate 1 with syringe bodies 3, and rack 4 with retained plungers 6 is then placed in a lyophilizer apparatus. The lyophilizer apparatus advantageously has therein a horizontally extending vertically movable pressing plate 18 which is controllably movable up and down by a suitable motor such as a cylinder within the lyophilizer apparatus. The cylinder is controllable from outside the apparatus. When the assembly of case 2, plate 1 and rack 4 is placed in the lyophilizer, this assembly is positioned beneath the pressing plate 18 which this time is at an elevated position above the button ends 21 of the plungers 6.

After placing the assembly of case, plate and rack in the lyophilizer apparatus, lyophilization is performed on the medicine, the lyophilization being assured by the spacing between the open upper ends of syringe bodies 3 and the pistons 5 in the rack 4. After the lyophilization phase, a sterile inert gas, for example, nitrogen, is introduced into the lyophilizer to establish a pressure in the lyophilizer which is lower than atmospheric pressure.

Then, the cylinder for operating the pressing plate 18 is actuated to move downwardly as shown at FIG. 8, to force plungers 6 downwardly so their pistons 5 are simultaneously pushed downwardly into the syringe bodies 3 through the upper ends of the syringe bodies. The pressing plate 18 is of sufficient length and width to simultaneously engage the button ends 21 of all the plungers 6, and has a length greater than upper rack 4, so that stop elements 19 and 20 at the opposite sides of rack 4 (FIG. 1) limit the extent of downward movement of the plate so that all the plungers are inserted the same predetermined distance into the syringe bodies.

After the plungers are inserted into the syringe bodies, the pressure in the lyophilizer is increased to atmospheric, preferably by introducing an inert gas such as nitrogen into the lyophilizer apparatus. When pressure equilibrium is attained, the lyophilizer is opened and the assembly of case 2, plate 1 and rack 4 is removed.

To remove the medicine-containing syringes, the two screws 15 and 16 (FIG. 3) are removed, to remove the clamp bar 14 from rack 4. A first cross-bar 7 is then removed and the first row of syringes containing the medicine can then be removed. After the second cross-bar 7 is removed, the second row of medicine-containing syringes can be removed, and this procedure is continued until all the cross-bars and syringes are removed from the assembly.

The medicine-containing syringes are then packaged under sterile conditions for distribution. While a preferred embodiment of the process and apparatus according to the invention has been shown and described, it is to be understood that changes can be made without departing from the scope and spirit of this invention.

We claim:

1. Process for simultaneously preparing a series of auto-injectable syringes containing a lyophile medicine, the syringes being of the type having a tubular body with an open upper end, and a lower end adapted to receive an injection needle, and an elongated plunger having a piston at its lower end which is insertable through the open upper end and frictionally slidable in the tubular body, said method comprising the steps of:
   sealing the lower ends of a number of tubular syringe bodies with a removable seal;
   positioning the syringe bodies vertically on a first flat horizontal rack so that the tubular bodies pass through holes of the first rack, and are held in the rack with their upper ends at the same level;
   filling a predetermined quantity of a solution of the medicine into each tubular body through the open upper end of the body;
   placing the same number of plungers in a second rack by introducing the piston ends of the plungers into holes of the second rack of a size to retain the pistons by friction;
   positioning the second rack retaining the plungers on the first rack holding the syringe bodies to form an assembly in which the holes of the second rack are coaxially aligned with the holes of the first rack and the piston ends of the plungers face toward and are axially aligned with but spaced above the upper ends of the syringe bodies so the upper ends of the syringe bodies are open;
   placing the assembly in a lyophilizer apparatus; performing lyophilization on the medicine in the syringes within the lyophilizer apparatus;
   then establishing a pressure lower than atmospheric pressure in the lyophilizer apparatus;
   then simultaneously forcing the plungers downwardly into the syringe bodies to move the pistons to a predetermined position in the bodies, above the lyophile medicine;
   then increasing the pressure in the lyophilizer to atmospheric pressure; and
   then removing the medicine-containing syringes from the lyophilizer, and from the racks, without removing the plungers from the pistons;
   said second rack comprising a plurality of disengageable cross-members being held in an operative position against each other by a removable clamp, said cross-members having vertical side wall along the length thereof with said vertical side walls having at spaced intervals half-holes formed therein whereby, when two of said cross-members are placed in juxtaposition, said half-holes, respectively, thereof, will face each other to define said holes of said second rack, said process further including the step of, after lyophilization, removing said medicine-containing syringes by sequentially removing said cross-members one-by-one.

2. Process according to claim 1, wherein the plungers are forced downwardly by a pressing plate in the lyophilizer apparatus.

3. Apparatus for simultaneously preparing a series of auto-injectable syringes containing a lyophile medicine, the syringes being of the type having a tubular body with an open upper end, and a lower end adapted to receive an injection needle, and an elongated plunger having a piston at its lower end which is insertable through the open upper end of and frictionally slidable in the tubular body, said apparatus comprising:
   a first flat rack having rows of identical holes for receiving therein the tubular bodies of the syringes and for holding the tubular bodies generally vertically, with their upper ends at the same level;
   means to hold the said first rack within a lyophilizer horizontally at a predetermined distance from a horizontal support.

a second flat rack with holes formed to correspond to each hole of the first rack when the two racks are superimposed, said holes of said second rack being of a dimension to frictionally retain a piston therein, with its plunger extending upwardly therefrom;

means for supporting the second rack within a lyophilizer at a fixed predetermined distance above the first rack with the holes of the second rack aligned with the holes of the first rack, so that said pistons enter and are forced downwardly into the tubular syringe bodies simultaneously, in response to simultaneously applying a downward force to upper ends of the plungers;

said second rack comprising a number of dismountable cross-members each having two vertical side walls and with half-holes formed in said vertical side walls and with said cross-members being mountable along side each other to extend substantially in a single plane whereby said half-holes define said holes of said second rack.

4. Apparatus according to claim 3, wherein each hole of the first rack is of a size slightly larger than the tubular syringe bodies to receive the bodies with slight play.

5. Apparatus according to claim 3, wherein the second rack is thick enough in the region of the holes for the sides of the holes to guide the pistons, during the beginning of the downward movement of the plungers, and until the pistons engage in the upper ends of the tubular syring bodies.

* * * * *